United States Patent [19]
Wilson

[11] Patent Number: 4,950,236
[45] Date of Patent: Aug. 21, 1990

[54] BREAST PUMP ADAPTER FOR FILLING INFANT NURSERS HAVING DISPOSABLE LINERS

[75] Inventor: Michael J. Wilson, Delta, Canada

[73] Assignee: Aurora Search Ltd., Delta, Canada

[21] Appl. No.: 260,865

[22] Filed: Oct. 21, 1988

[51] Int. Cl.$^5$ .............................................. A61M 1/06
[52] U.S. Cl. ...................................... 604/74; 215/115
[58] Field of Search ................................... 604/74–76, 604/313, 316, 347; 215/11.1, 11.3, 11.5

[56] References Cited

U.S. PATENT DOCUMENTS

| | | |
|---|---|---|
| 2,542,505 | 2/1951 | Gascoigne .............................. 604/74 |
| 3,977,405 | 8/1976 | Yanase ................................... 604/74 |
| 4,238,040 | 12/1980 | Fitzpatrick ......................... 215/11.3 |
| 4,673,388 | 6/1987 | Schlensog et al. ..................... 604/74 |
| 4,705,504 | 11/1987 | Viers ..................................... 604/75 |
| 4,759,747 | 7/1988 | Aida et al. ............................. 604/74 |

*Primary Examiner*—Jerome L. Kruter
*Attorney, Agent, or Firm*—Spensley Horn Jubas & Lubitz

[57] ABSTRACT

Infant nursers use a disposable, flexible plastic liner in a rigid, reusable shell. Previously, it has been the practice when breast pumps are used to pump the breast milk into an intermediate storage container and then pour it into the disposable liner of the nurser, or another intermediate container for freezing. The present invention provides an adapter for use with existing breast pumps which allows the breast milk to be pumped directly into the liner of the nurser without the need for any valves or moving parts. The adapter snaps onto the existing nipple-retaining cap and uses the liner of the nurser itself to form a valve. In a second embodiment, the adapter is provided with a unitary threaded circular rim to attach directly to the threaded end of the nurser shell.

12 Claims, 7 Drawing Sheets

BREAST PUMP ADAPTER FOR FILLING INFANT NURSERS HAVING DISPOSABLE LINERS

BACKGROUND OF THE INVENTION

The present invention relates to the field of breast pumps and more particularly to an adapter for allowing existing breast pumps to fill infant nursers having disposable liners.

The combination of an increased awareness of the health benefits of breast-feeding an infant and the increased number of women returning to the work force shortly after giving birth has led to an increased use of breast pumps for maintaining a supply of breast milk for the infant when the mother is unavailable. Banks of donors' breast milk have also been established to nourish needy infants. A wide variety of types of breast pumps is available, both manual and electrically operated. The most effective breast pumps provide alternating positive and negative pressure at 45 to 60 cycles per minute to simulate the sucking action of the infant. Most such pumps provide a receptacle for temporarily receiving the extracted milk. The milk is then transferred to the baby bottle or to a freezer container for freezing and long term storage.

Infant nursers, such as those manufactured and sold under the PLAYTEX trademark, consisting of a disposable polyethylene plastic liner fitted inside a rigid, reusable plastic shell, have become very popular due the convenience and added cleanliness and safety which comes from not having to wash and reuse the baby's bottle. Disposable bags of a nylon/polyethylene laminate have also been developed to reduce the loss of nutrients when the milk is stored over a long period of time. Where the mother wishes to utilize a nurser to feed her own breast milk to her child, it has been necessary for the mother to express the milk by hand into the disposable liner or use a breast pump and transfer the extracted milk by hand from the pump container to the nurser. Both procedures are time-consuming, messy and unsanitary.

One breast pump known to the inventor, disclosed in U.S. Pat. No. 4,705,504, issued Nov. 10, 1987 to Viers, uses a disposable, removable bag to receive the pumped milk, but this design involves using a squeezable rubber bulb to create the negative pumping pressure, and the disposable bag is held onto the rubber bulb by an elastic band. The bag has no rigid support. Consequently this pump is difficult and inefficient to use and still requires that the user transfer the filled bag of milk to the nurser or some other dispenser.

There is therefore a need for an effective adapter which allows existing breast pumps to be used to fill infant nursers directly.

SUMMARY OF THE INVENTION

The present invention provides an adapter for filling infant nursers from a breast pump. The adapter comprises a breast shield adapted to receive a female breast, a storage reservoir communicating at its upper end with and extending downwardly from the shield and substantially closed at its lower end by a surface extending obliquely to the plane normal to the longitudinal direction of the reservoir, and an air inlet communicating with the reservoir for connecting the pump. The air inlet may be shielded by a baffle. According to one embodiment, there is a resilient clip extending from the exterior wall of the reservoir near the upper end thereof and beneath the shield for releasably securing the adapter to the lip of the nipple-retaining cap. The closed end of the reservoir has a groove across its upper portion for seating on the lip of the nipple-retaining cap of the nurser and a hole for the passage of milk. In a second embodiment the adapter has a threaded circular rim moulded as a unitary part of it, and which threads onto the end of the nurser shell.

BRIEF DESCRIPTION OF THE DRAWINGS

In drawings which illustrate a preferred embodiment of the invention.

DETAILED DESCRIPTION OF A PREFERRED EMBODIMENT

Figure 1:
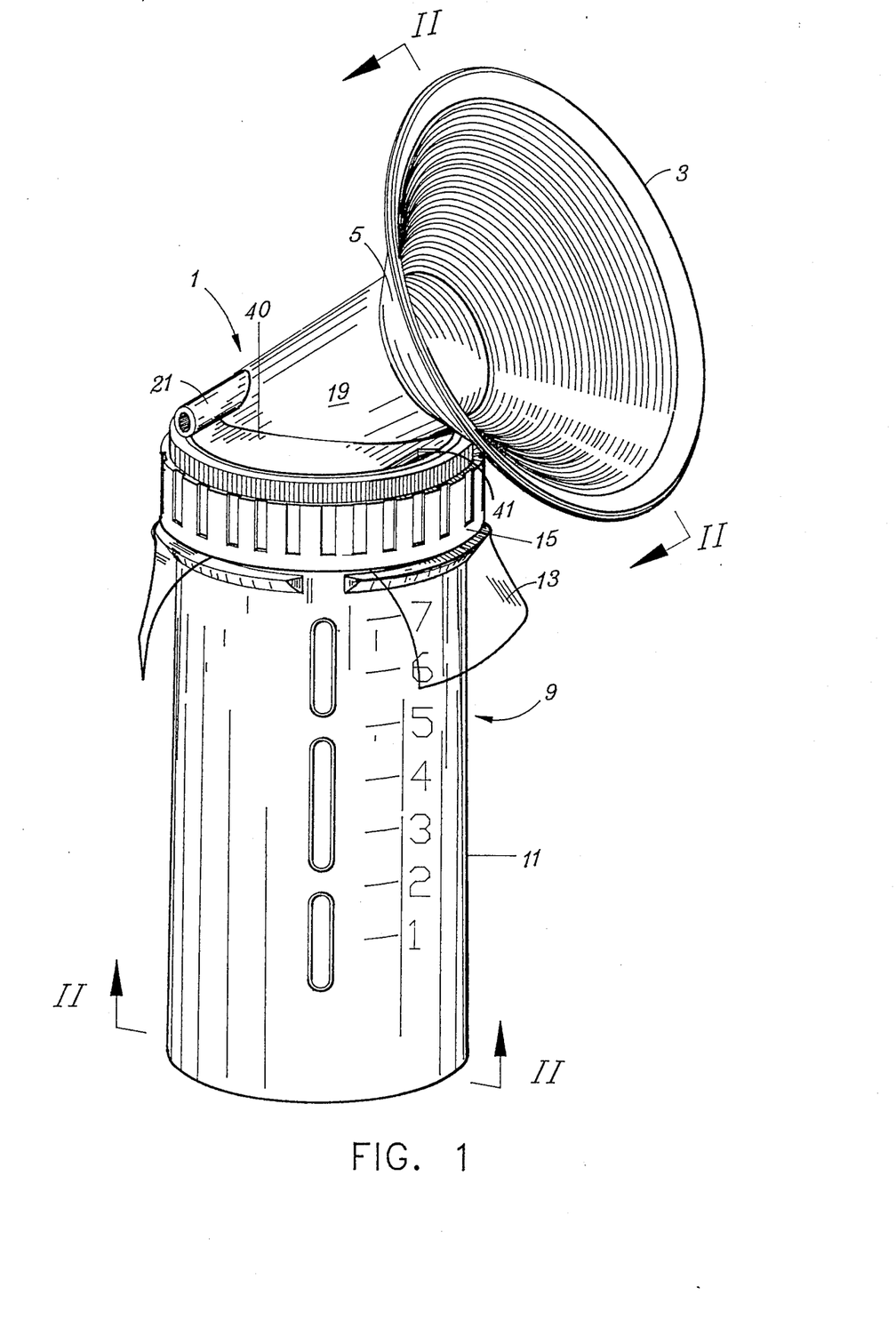
FIG. 1 is a perspective view of a first embodiment of the invention installed on an infant nurser.
Figure 2:
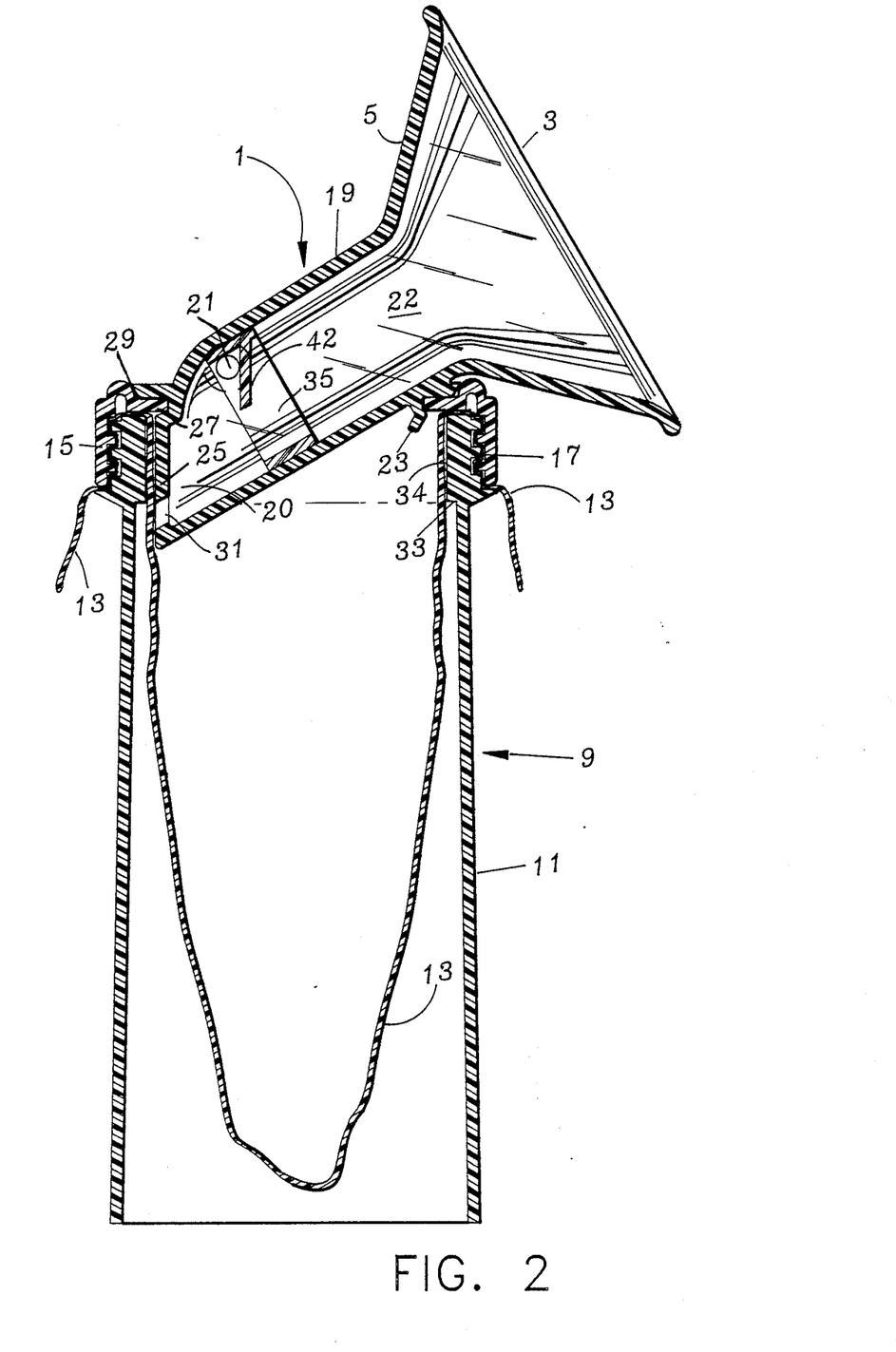
FIG. 2 is a cross-section along lines II—II of FIG. 1.
Figure 3:
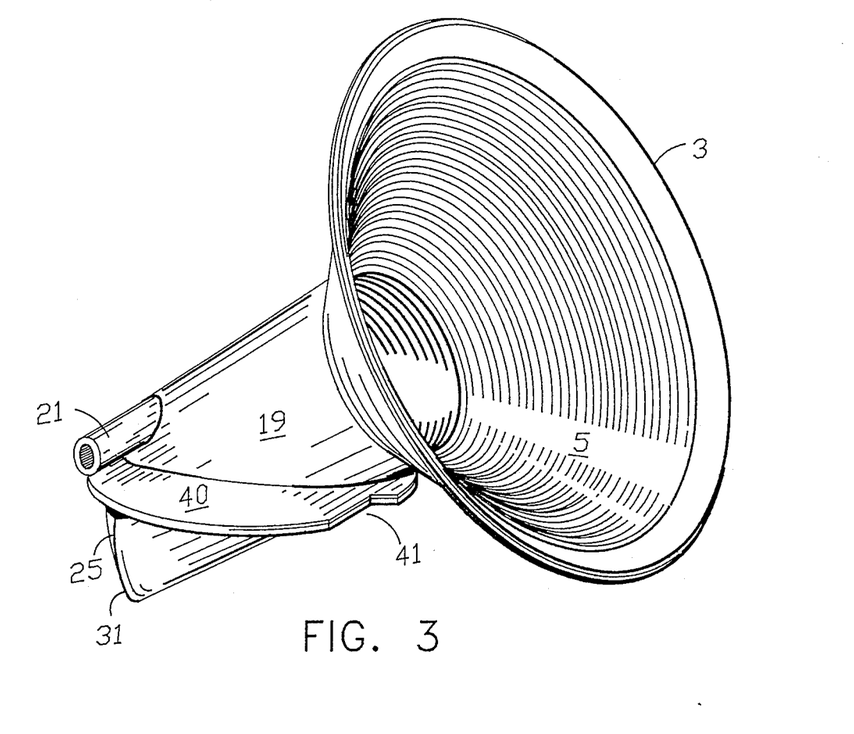
FIG. 3 is a perspective view of the adapter of the invention separated from the nurser.
Figure 4:
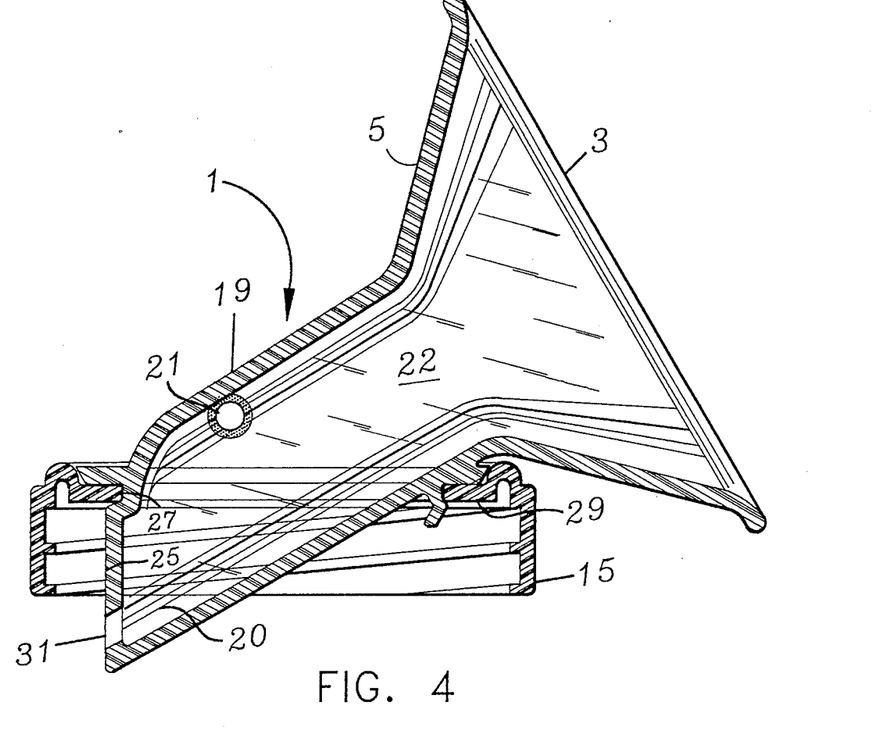
FIG. 4 is a detail of the cross-section of FIG. 2 with nurser and baffle removed and nipple-retaining cap attached.

The adapter of the invention is designated generally by reference numeral 1. It includes a plastic breast shield 3 of existing design which has a conical section 5 which is pressed against the female breast. The adapter is shown in FIGS. 1 and 2 installed on a standard infant nurser 9, such as that sold under the trademark PLAYTEX, which consists of a cylindrical, rigid plastic shell 11 and a disposable liner 13 of flexible polyethylene film. Laminates of nylon and polyethylene are also used for the disposable liner. The bottle has a circular cap 15 which is threaded onto threaded end 17 in the upper outer surface of the shell and normally retains the rubber nipple in the opening of the nurser. The central area of cap 15 is thus open, leaving a horizontally-extending annular rim 29. The upper edge of the liner is held in place between the cap 15 and shell 11 when cap 15 is screwed onto threaded end 17 over the liner. Around the inner, upper edge of the shell 11 in such nursers in the area of the threaded end 17, there is an inwardly projecting horizontal ledge 33 meeting inner surface 34.

The adapter has a cylindrical section 19 which forms a lower reservoir section 20 and an upper neck section 22. Projecting horizontally from the upper edge of the reservoir section is a connecting tube 21 to which the pumping source of alternating higher and lower pressure or modulated negative pressure is attached. Projecting downwardly from the lower surface of the upper neck section is a resilient clip 23. A circular cover flange 40 extends horizontally from the cylindrical section 19. This flange covers the open areas of the mouth of the nurser when the adapter is installed to prevent the entry of foreign matter into the milk being collected. It has an opening 41 to allow air to escape from the nurser liner as it is filled.

The lower end of the reservoir 20 is substantially closed off by a curved surface 25 which cuts obliquely across the reservoir section as shown in FIG. 2 so that when surface 25 is parallel to the curved vertical sides of shell 11, the axis of the cylindrical section 19 forms an acute angle with the horizontal. A slot or groove 27 is provided across the upper edge of surface 25 to receive the inner lip 29 of cap 15. A hole 31 is formed in the lower part of the surface 25, typically of about ⅛" to ¼" in diameter. The dimension of cylindrical section 19 is chosen so that the hole 31 is located below the ledge 33. Thus while the flexible liner 13 is in contact with both surface 34 and surface 25 in the area above hole 31, the liner has a slight freedom of movement in the horizontal direction in the vicinity of hole 31. Surface 25 conforms in curvature to that of the shell 11 and has rounded edges to allow the cap 15 to be screwed or unscrewed onto or off of end 17 with the adapter installed on the cap.

Figure 5:
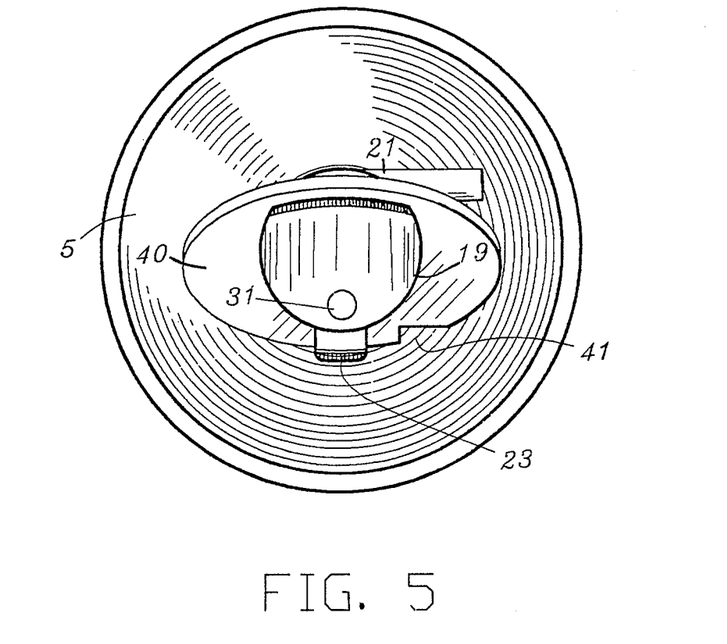
FIG. 5 is a rear view of the adapter shown in FIG. 3.
Figure 6:
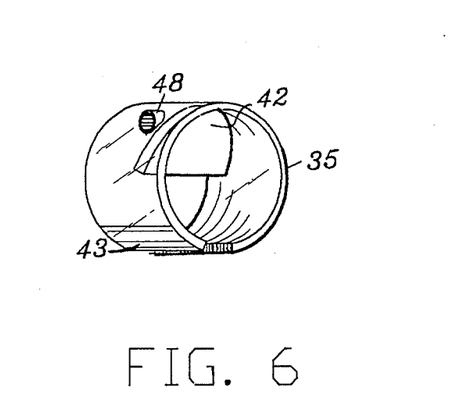
FIG. 6 is a perspective view of the removable baffle insert of the invention.
Figure 7:
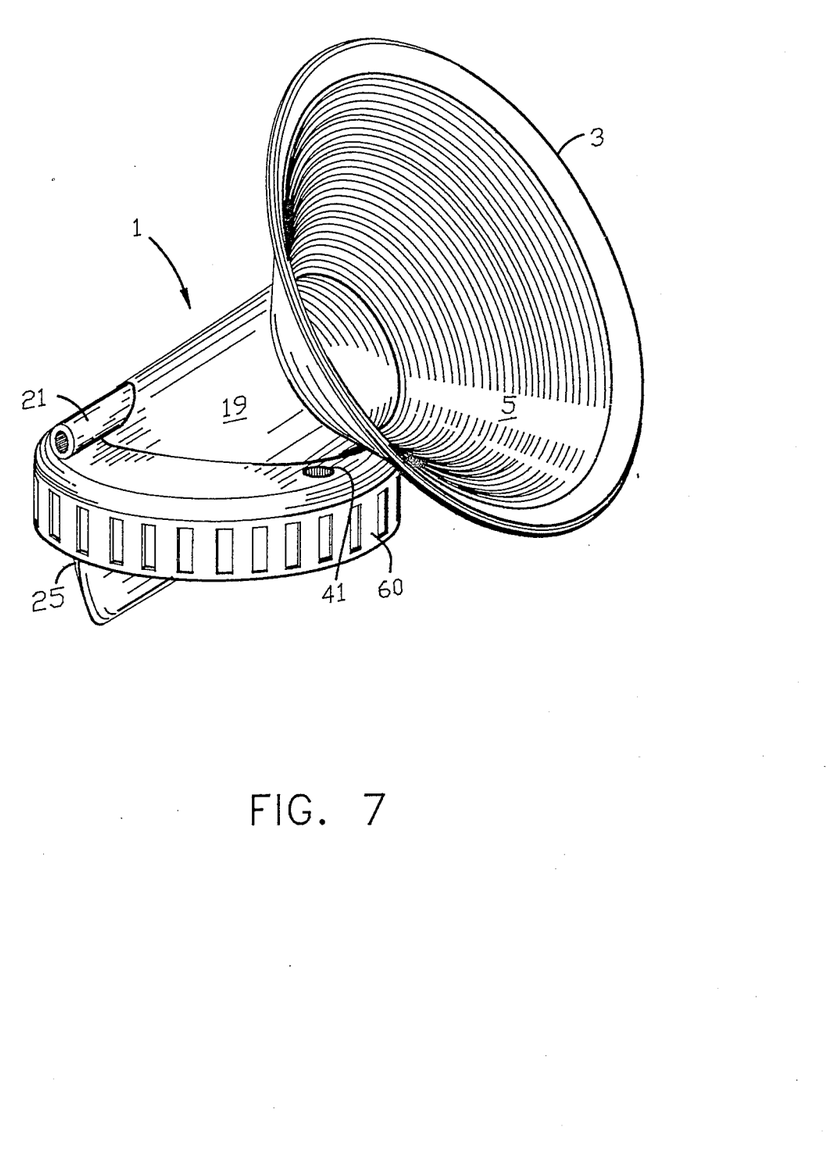
FIG. 7 is a perspective view of a second embodiment of the invention.
Figure 8:
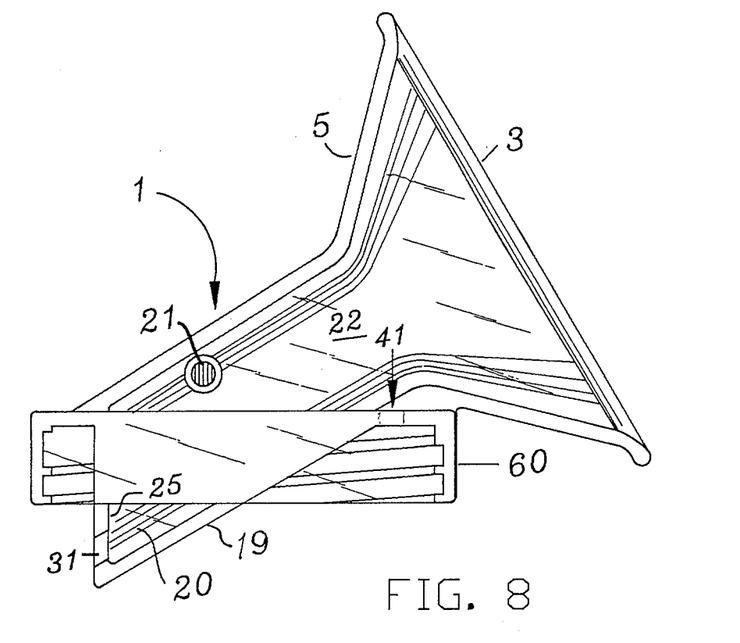
FIG. 8 is a side view of the embodiment shown in FIG. 7.
Figure 9:
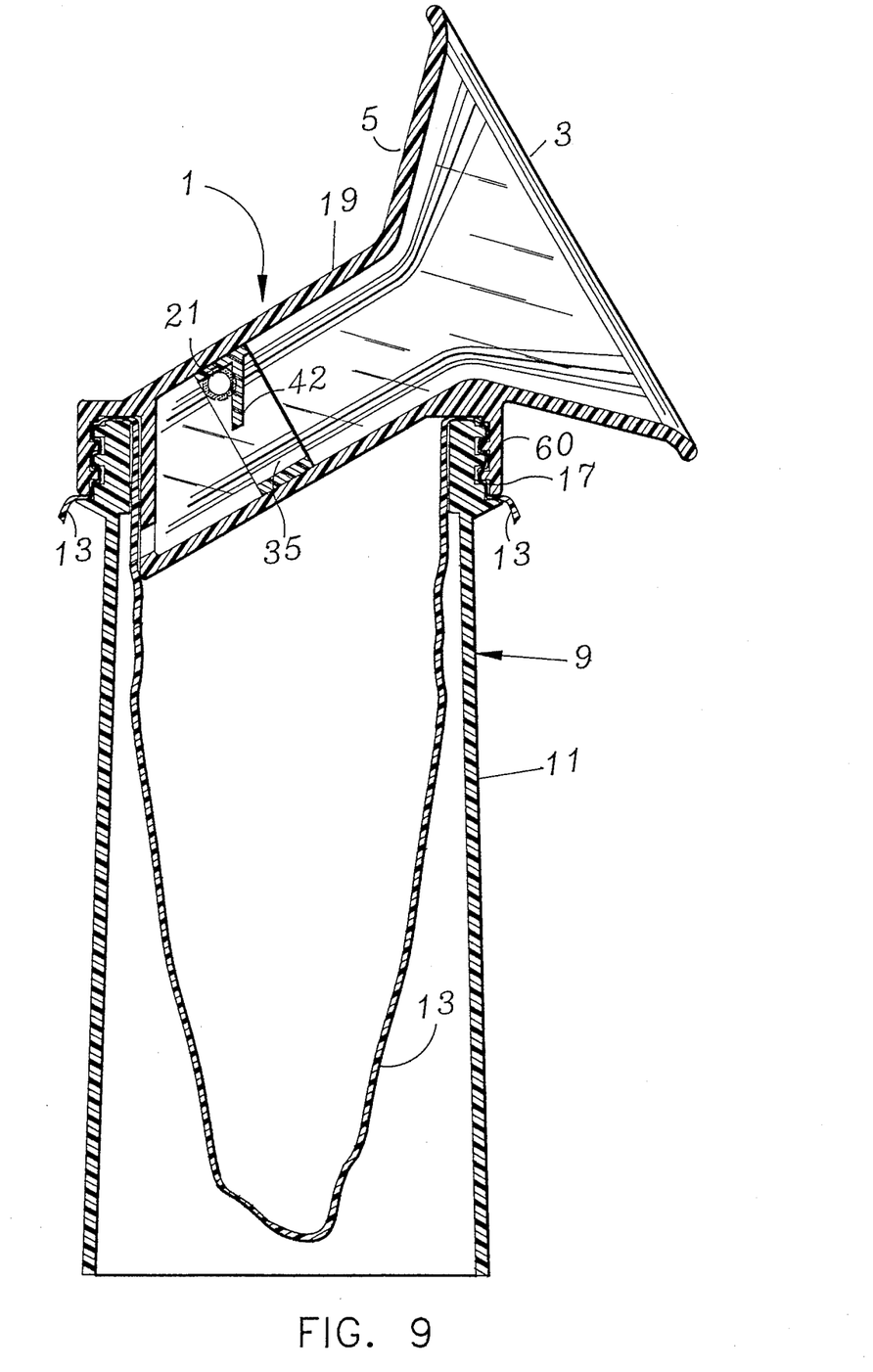
FIG. 9 is a vertical cross-section of the embodiment shown in FIG. 7 installed on a nurser.
Figure 10:
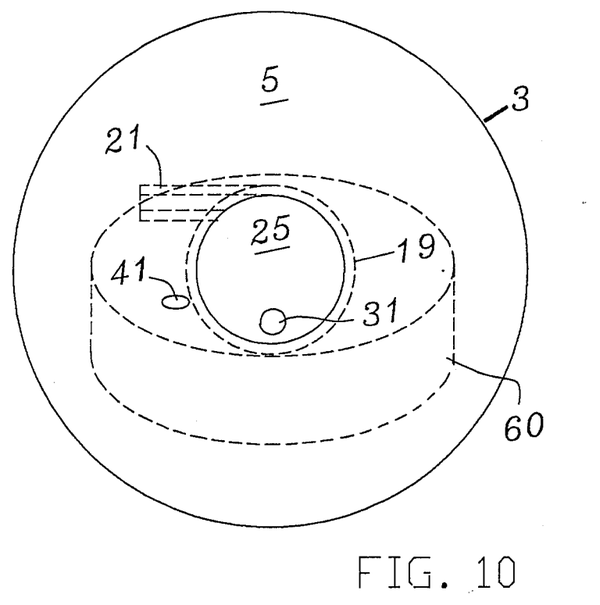
FIG. 10 is a plan view looking into the breast shield of the adapter shown in FIG. 7.

In order to prevent the splashing of milk into the air outlet 21, a removable baffle 35 shown in FIGS. 2 and 5 may be provided which shields the inlet. The baffle is preferably removable for ease of cleaning. It has a circular plastic ring 43 to which is attached a shield plate 42 which extends to cover about one-half of the diameter of the cylindrical section. The plate 42 is attached at an angle to the ring so that it is roughly parallel to surface 25 when installed. In this way, milk is directed downwardly towards the nurser rather than being splashed back at the breast. The ring 43 has a lower slit to allow flow of milk and to make the circumference flexible, and a hole 48 which aligns with the hole for inlet 21. A thin projecting ridge 49 around the outside edge of hole 48 is aligned to extend into the hole for air inlet 21 and thus holds the baffle in place in the adapter. By making the diameter of the baffle insert slightly greater than the inner diameter of cylindrical section 19, the insert is held in place by friction.

In use, the liner 13 is placed in position in nurser shell 11, the edge of the liner is stretched over threaded end 17 and the nipple-retaining cap 15 is threaded over the threaded end 17 of the shell 11 and the upper edge of liner 13, securing the liner in place. The breast pump, whether electric or manual, is connected to inlet 21 by a hose or other suitable means of connection. Groove 27 is then placed over rim 29 and adapter 1 is snapped into a firm friction fit with the rim 29 by rotating the shield end of the adapter downwardly, bringing resilient clip 23 into contact with the rim 29 and causing it to snap over the rim as the adapter is further pressed down. In this position the cover flanges 40 rest snugly against the upper surface of rim 29 and serve to stabilize the adapter as well as preventing the entry of foreign matter.

The breast may then be positioned within cone 5 for milk extraction. When negative pressure is applied to inlet 21, the flexible liner 13 is drawn against surface 25 and seals hole 31, and milk collects in the lower part of reservoir 20. When positive pressure is applied, liner 13 is forced away from hole 31 and the milk flows into the liner 13. Air is able to be displaced from the liner through opening 41 in flange 40. The seal formed between the liner and surface 25 on the negative pressure stroke is somewhat imperfect, but this is in fact desirable for the breast pump application since too great a period of suction on the breast without relief can rupture the nipple skin. The choice of breast pump used with the adapter will of course determine the length and degree of the negative pressure portion of the cycle.

A similar action takes place where the type of breast pump used does not provide cycles of alternating positive and negative pressure, but rather only intermittent negative cycles. Rather than the milk held in reservoir 20 being forced through hole 31 on the positive portion of the cycle, the milk simply flows through the hole by gravity when the negative pressure is released.

In the second embodiment of the invention shown in FIGS. 7 through 10, the adapter is moulded in a unitary piece with a threaded circular rim 60. To use this variation of the invention, the liner 13 is placed in position in the nurser shell 11, the edge of the liner is stretched over threaded end 17 and the rim portion 60 of the adapter is threaded down over the edge of the liner to secure the liner for filling. Otherwise the second embodiment operates in the same manner as the first embodiment.

As will be apparent to those skilled in the art, various modifications and adaptations of the structure above described may be made without departing from the spirit of the invention, the scope of which is to be construed in accordance with the accompanying claims.

I claim:

1. An adapter for filling infant nursers from a breast pump, where said infant nurser comprises a flexible, liquid-containing liner supported in a solid shell, said adapter comprising:

(a) a breast shield adapted to receive a female breast;
(b) a hollow chamber communicating at its upper end with and extending downwardly from said shield and substantially closed at its lower end, and having an extension of said lower end comprising an aperture for the passage of milk;
(c) an air passageway communicating with said hollow chamber for connecting a pump; and
(d) means for fixing said adapter relative to a flexible liner supported in a nurser wherein said extension is placed in sufficiently close proximity to a section of said flexible liner to thereby cause said section of said flexible liner to be releasably drawn toward and to cover said aperture upon a temporary reduction of pressure in said hollow chamber caused by a pump, thereby restricting the flow of air through said aperture, sufficiently quickly to prevent significant reduction of pressure in the interior of said flexible liner and to be released from said aperture upon a temporary increase of pressure in said hollow chamber;

and wherein said nurser comprises a nipple-retaining cap having a central opening forming an inner annular lip and said means for fixing comprises:

(e) clip means extending from the exterior wall of said chamber near the upper end thereof and beneath said shield for releasably securing said adapter to said lip of said nipple-retaining cap; and
(f) a groove in said adapter adapted for seating on the inner edge of said inner annular lip;

and further comprising flange means extending horizontally from said hollow chamber and adapted to contact the upper surface of said lip of said nipple-retaining cap, wherein said flange is provided with an aperture for the passage of air between the exterior of the adapter and the interior of said flexible liner.

2. The adapter of claim 1 wherein said extension of said lower end comprises a surface lying substantially parallel to the wall of said flexible liner and said aperture for the passage of milk is formed in said surface.

3. A collecting and storage apparatus for extracting milk from a breast using a breast pump, comprising:
   (a) an infant nurser comprising a solid shell and a flexible liquid-containing liner supported in said solid shell; and
   (b) an adapter for filling said nurser from said pump, said adapter comprising:
      (i) a breast shield adapted to receive a female breast;
      (ii) a hollow chamber communicating at its upper end with and extending downwardly from said shield and substantially closed at its lower end, and having an extension of said lower end comprising an aperture for the passage of milk;
      (iii) an air passageway communicating with said hollow chamber for connecting said pump; and
      (iv) means for fixing said adapter relative to a flexible liner supported in a nurser wherein said extension is placed in sufficiently close proximity to a section of said flexible liner to thereby cause said section of said flexible liner to be releasably drawn toward and to cover said aperture upon a temporary reduction of pressure in said hollow chamber caused by a pump, thereby restricting the flow of air through said aperture, sufficiently quickly to prevent significant reduction of pressure in the interior of said flexible liner and to be released from said aperture upon a temporary increase of pressure in said hollow chamber;
   further comprising a pump for providing modulated pressure reduction and means for communicating said pressure reduction between said pump and said adapter;
   and wherein said adapter further comprises removable baffle means adapted to removably shield said air passageway, comprising an annular ring adapted to slide within said hollow chamber and a planar surface extending across the centre of said annular ring in a location to shield said air passageway.

4. The apparatus of claim 3 wherein said pump provides alternating positive and negative pressure to said hollow chamber.

5. The adapter of claim 3 wherein said means for securing comprises a circular cap secured to said hollow chamber and adapted to be removably attached to said container, and provided with an aperture to allow the passage of air from said container.

6. A collecting and storage apparatus for extracting milk from a breast using a breast pump providing a modulating pressure, comprising:
   (a) an infant nurser comprising a solid shell and a flexible liquid-containing liner supported in said solid shell, the interior of said liner communicating with the atmosphere outside of said shell to allow the passage of air therebetween; and
   (b) an adapter for filling said nurser from said pump, said adapter comprising:
      (i) a breast shield adapted to receive a female breast;
      (ii) a hollow chamber communicating at its upper end with and extending downwardly from said shield and substantially closed at its lower end, and having an extension of said lower end comprising an aperture for the passage of milk;
      (iii) an air passageway communicating with said hollow chamber for connecting said pump; and
      (iv) means for fixing said adapter relative to said flexible liner supported in said nurser wherein said extension is placed in sufficiently close proximity to a section of said flexible liner to thereby cause said section of said flexible liner to be releasably drawn toward and to cover said aperture for the passage of milk upon a temporary reduction of pressure in said hollow chamber caused by said pump, thereby restricting the flow of aid through said aperture, sufficiently quickly to prevent significant reduction of pressure in the interior of said flexible liner and to be released from said aperture upon a temporary increase of pressure in said hollow chamber.

7. The adapter of claim 6 wherein said means for fixing comprises a flange secured to said adapter and adapted to be removably attached to said nurser, and provided with an aperture to allow the passage of air from said flexible liner.

8. The apparatus of claim 7 wherein said nurser comprises a nipple-retaining cap having a central opening forming an inner annular lip and said means for fixing comprises a groove in said adapter adapted for seating on the inner edge of said inner annular lip.

9. The apparatus of claim 8 wherein said means for fixing further comprises clip means extending from the exterior wall of said hollow chamber near the upper end thereof and beneath said shield for releasably securing said adapter to said lip of said nipple-retaining cap.

10. The apparatus of claim 6 wherein said pump provides alternating positive and negative pressure to said adapter.

11. The apparatus of claim 6 wherein said adapter further comprises removable baffle means adapted to removably shield said air passageway, comprising an annular ring adapted to slide within said hollow chamber and a planar surface extending across the centre of said annular ring in a location to shield said air passageway.

12. The adapter of claim 6 wherein said means for fixing comprises a circular cap secured to said adapter and adapted to threadedly engage said nurser and provided with an aperture to allow the passage of air from said flexible liner.

* * * * *

UNITED STATES PATENT AND TRADEMARK OFFICE
CERTIFICATE OF CORRECTION

PATENT NO. : 4950236

DATED : August 21, 1990

INVENTOR(S) : Michael J. Wilson

It is certified that error appears in the above-identified patent and that said Letters Patent is hereby corrected as shown below:

In claim 6, column 6 line 23, the word "aid" should read --air--.

Signed and Sealed this

Tenth Day of December, 1991

Attest:

HARRY F. MANBECK, JR.

*Attesting Officer*        *Commissioner of Patents and Trademarks*